(12) United States Patent
Spangler et al.

(10) Patent No.: US 9,687,356 B1
(45) Date of Patent: Jun. 27, 2017

(54) SPINAL FUSION IMPLANTS AND RELATED METHODS

(71) Applicant: NuVasive, Inc., San Diego, CA (US)

(72) Inventors: Jonathan Spangler, Del Mar, CA (US); Neil Warren, Redwood City, CA (US)

(73) Assignee: NuVasive, Inc., San Diego, CA (US)

( * ) Notice: Subject to any disclaimer, the term of this patent is extended or adjusted under 35 U.S.C. 154(b) by 329 days.

(21) Appl. No.: 13/648,253

(22) Filed: Oct. 9, 2012

Related U.S. Application Data

(60) Provisional application No. 61/545,066, filed on Oct. 7, 2011.

(51) Int. Cl.
*A61F 2/44* (2006.01)

(52) U.S. Cl.
CPC ............ *A61F 2/4455* (2013.01); *A61F 2/447* (2013.01); *A61F 2002/4415* (2013.01)

(58) Field of Classification Search
CPC ........ A61F 2/4455; A61F 2/447; A61F 2/448; A61F 2/4485; A61F 2002/4415
USPC ............................................. 623/17.11–17.16
See application file for complete search history.

(56) References Cited

U.S. PATENT DOCUMENTS

| | | | |
|---|---|---|---|
| 5,522,899 A * | 6/1996 | Michelson | A61F 2/30744 606/279 |
| 6,387,130 B1 * | 5/2002 | Stone | A61F 2/4455 623/17.16 |
| 6,942,697 B2 * | 9/2005 | Lange | A61F 2/447 623/17.11 |
| 6,986,788 B2 * | 1/2006 | Paul | A61F 2/28 623/17.11 |
| 6,989,031 B2 * | 1/2006 | Michelson | A61F 2/28 623/17.11 |
| 7,192,447 B2 * | 3/2007 | Rhoda | A61F 2/442 623/17.11 |
| 7,455,692 B2 * | 11/2008 | Michelson | A61F 2/4455 623/17.11 |
| 7,867,277 B1 * | 1/2011 | Tohmeh | A61F 2/4455 623/17.11 |
| 8,025,697 B2 * | 9/2011 | McClellan, III | A61F 2/4455 623/17.11 |
| 8,512,408 B2 * | 8/2013 | Miller | A61F 2/4425 623/17.16 |
| 2003/0125739 A1 * | 7/2003 | Bagga | A61F 2/4455 606/247 |
| 2006/0142858 A1 * | 6/2006 | Colleran | A61F 2/4465 623/17.11 |
| 2006/0189999 A1 * | 8/2006 | Zwirkoski | A61F 2/442 606/90 |
| 2007/0067035 A1 * | 3/2007 | Falahee | A61F 2/4455 623/17.11 |
| 2007/0191951 A1 | 8/2007 | Branch | |
| 2007/0260314 A1 * | 11/2007 | Biyani | A61F 2/4465 623/17.11 |

(Continued)

*Primary Examiner* — Ellen C Hammond
(74) *Attorney, Agent, or Firm* — Jeremy A. Smith; Timothy L. Capria; Bradley Arant Boult Cummings LLP

(57) ABSTRACT

A system and methods for promoting fusion across an intervertebral disc space, the system including a plurality of spinal fusion implants wherein the maximum length of an individual implant less than the maximum depth dimension of the endplate of the inferior vertebral body into which the system of spinal fusion implants is inserted.

9 Claims, 12 Drawing Sheets

(56) References Cited

U.S. PATENT DOCUMENTS

| | | | |
|---|---|---|---|
| 2008/0221687 A1* | 9/2008 | Viker | A61F 2/4455 623/17.16 |
| 2008/0249628 A1* | 10/2008 | Altarac | A61F 2/4455 623/17.16 |
| 2009/0143859 A1* | 6/2009 | McClellan, III | A61F 2/4455 623/17.16 |
| 2009/0182431 A1* | 7/2009 | Butler | A61F 2/447 623/17.16 |
| 2009/0240335 A1* | 9/2009 | Arcenio | A61B 17/7094 623/17.16 |
| 2011/0029083 A1* | 2/2011 | Hynes | A61F 2/447 623/17.16 |
| 2011/0029085 A1* | 2/2011 | Hynes | A61F 2/4611 623/17.16 |
| 2011/0125266 A1* | 5/2011 | Rodgers | A61F 2/447 623/17.11 |
| 2011/0320000 A1 | 12/2011 | O'Neil et al. | |
| 2011/0321000 A1* | 12/2011 | Fujimori | G06F 17/5036 716/136 |

* cited by examiner

SPINAL FUSION IMPLANTS AND RELATED METHODS

CROSS REFERENCE TO RELATED APPLICATIONS

This application claims the benefit of the filing date of U.S. Provisional Application No. 61/545,066, which was filed on Oct. 7, 2011. The contents of U.S. Application No. 61,545,066 are incorporated by reference in their entirety as a part of this application.

BACKGROUND

The present application relates to spinal fusion surgery, and more particularly, to a system for promoting fusion across an intervertebral disc space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
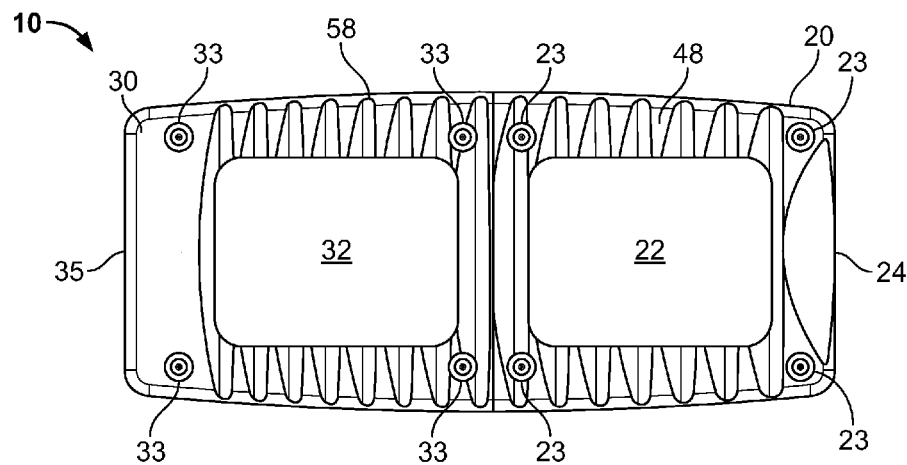
FIGS. 1-7 illustrate a system of implants for promoting fusion across an intervertebral disc space according to a first embodiment.
Figure 2:
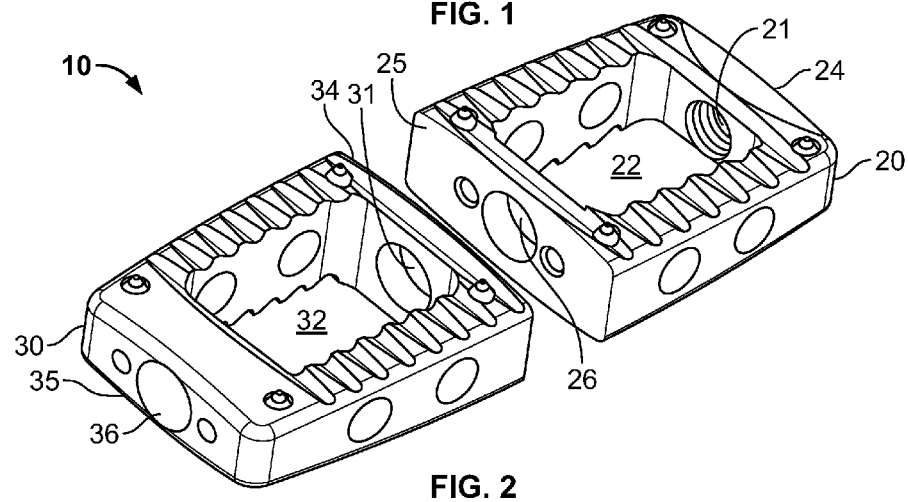
Figure 3:
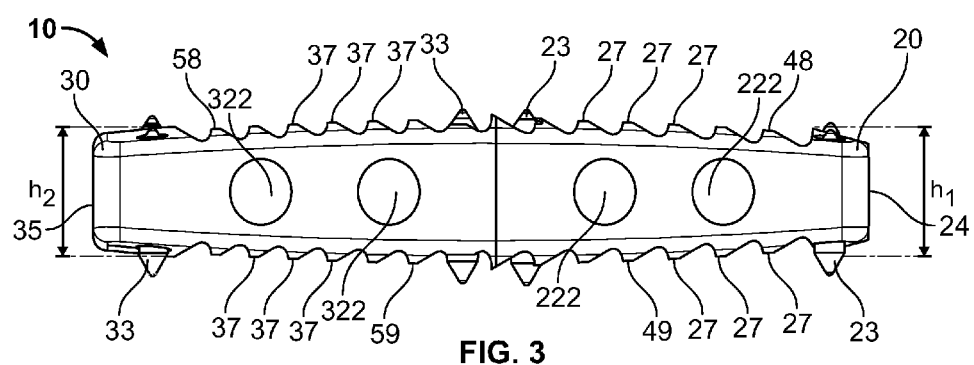
Figure 4:
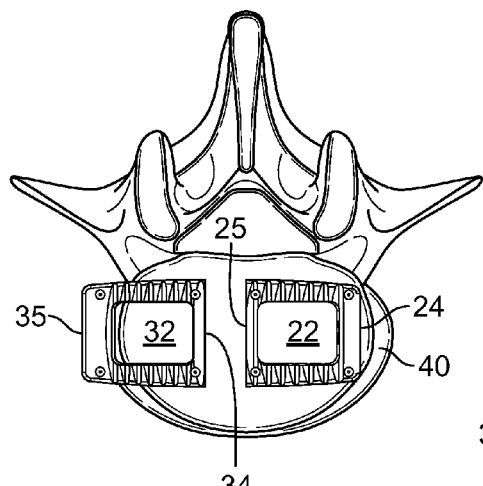
Figure 5:
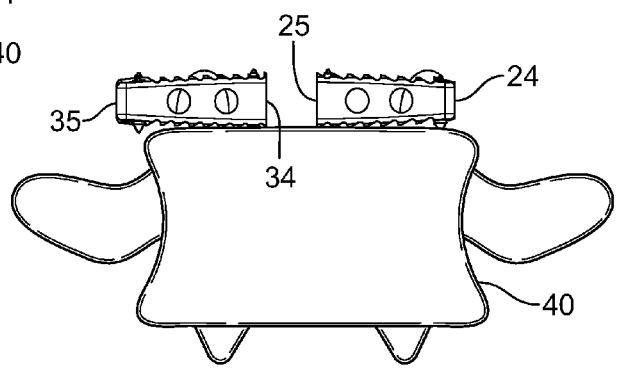
Figure 6:
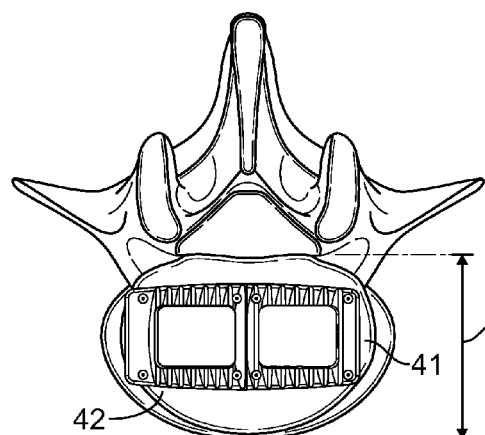
Figure 7:
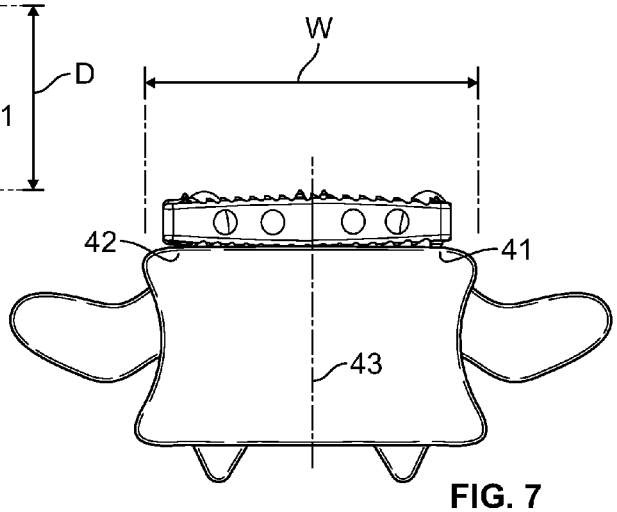
Figure 8:
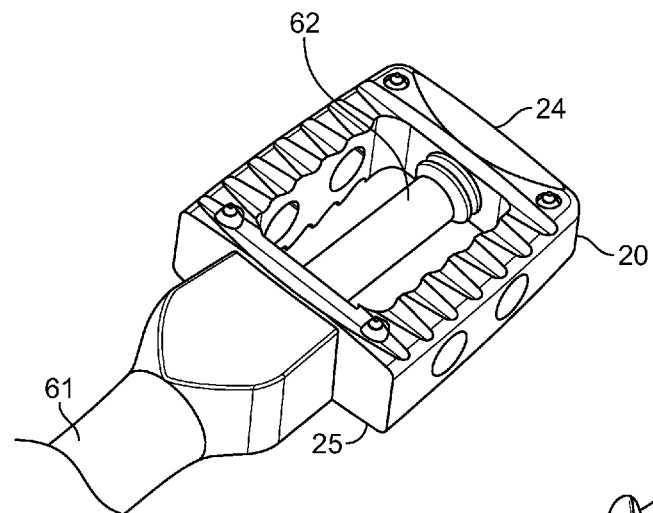
FIGS. 8-13 illustrate a system and method of inserting implants for promoting fusion across an intervertebral disc space according to the first embodiment.
Figure 9:
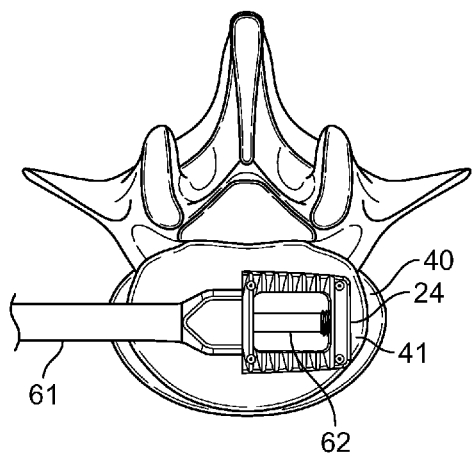
Figure 10:
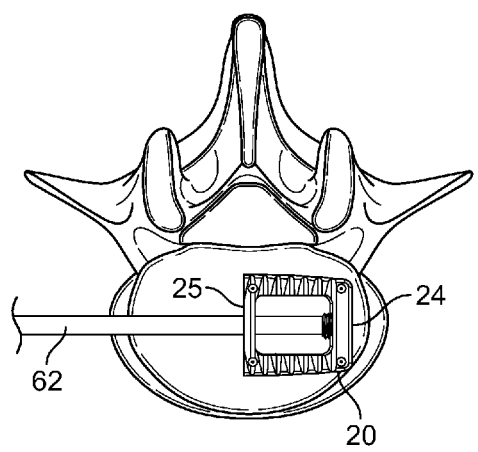
Figure 11:
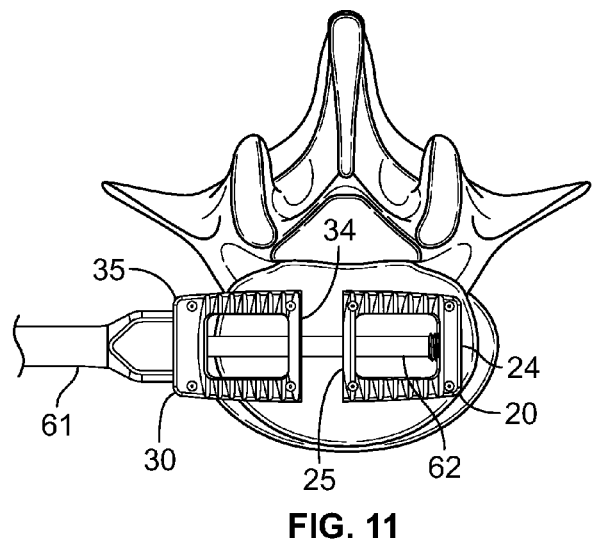
Figure 12:
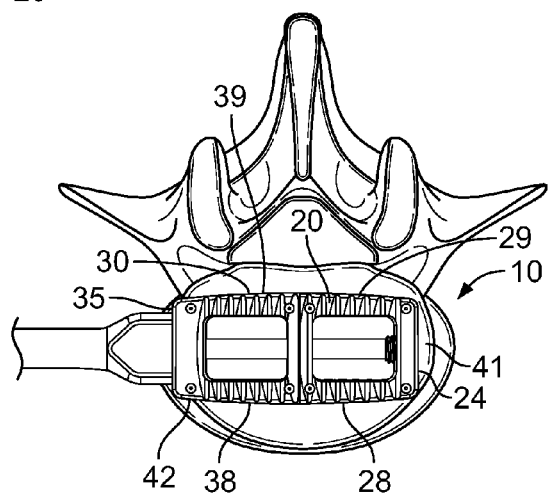
Figure 13:
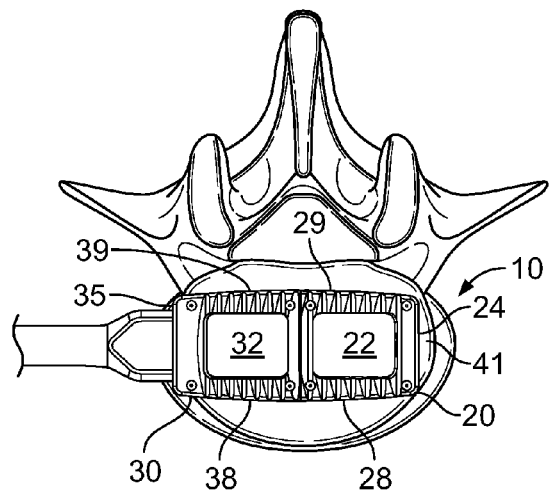

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and methods for promoting fusion across an intervertebral disc space disclosed herein boasts a variety of inventive features and components that warrant patent protection, both individually and in combination.

FIGS. 1-7 illustrate a system 10 for promoting fusion across an intervertebral disc space according to an exemplary embodiment. The system 10 includes a first intervertebral fusion implant 20 and a second intervertebral fusion implant 30, both dimensioned for insertion into an intervertebral disc space via lateral approach. The system of implants 10 is dimensioned such that the distal end of the first implant 20 rests on a first lateral aspect 41 of a vertebral body 40 and the proximal end of the second implant 30 rests on the opposite, second lateral aspect 42 of a vertebral body 40 when the system is fully inserted within an intervertebral disc space. Each of the first implant 20 and second implant 30 includes a top surface 48, 58, a bottom surface 49, 59, and a fusion aperture 22, 32 extending between the top surface 48, 58 and bottom surface 49, 59. Each of the first and second implants 20, 30 have an anterior wall 28, 38 and a posterior wall 29, 39 and a leading end wall 24, 34 and a trailing end wall 25, 35 walls defining the perimeter of the fusion apertures 22, 32. According to one aspect, each of the first and second implants 20, 30 include anti-migration features 27, 37 on one or both of the top surface 48, 58 and bottom surface 49, 59. The exemplary implants 20, 30 also include radiopaque markers 23, 33 proximate the leading end 24, 34 and trailing end 25, 35 to aid in positioning during implantation. Each of the first implant 20 and second implant 30 are constructed of biocompatible material.

According to the exemplary embodiment shown in FIGS. 1-7, the first implant 20 and second implant 30 are mirror images of each other, having equal height and length, wherein the length of each of the first and second implant 20, 30 is less than or equal to half of the maximum width dimension W of the endplate of the inferior vertebral body 40 adjacent the intervertebral disc space into which the system of implants 10 is inserted, the width dimension W being measured from a first lateral aspect 41 to the opposite second lateral aspect 42 of the vertebral body. However, the implants 20, 30 may have different lengths, but each of the first and second implant will have a maximum length that is less than the depth dimension D of the endplate of the inferior vertebral body 40 adjacent the intervertebral space into which the system of implants 10 is inserted, wherein the depth dimension D is measured from an anterior aspect of the endplate of the inferior vertebral body to a posterior aspect of the endplate of the inferior vertebral body. Similarly, while the first and second implants 20, 30 shown in FIGS. 1-7 have an equal height $h_1$, $h_2$ measured from the top surface 48,58 to the bottom surface 49, 59 of the implant 20, 30, the height $h_1$ of the first implant 20 may be greater than the height $h_2$ of the second implant 30, or vice versa. Each implant may also have an anterior wall 28, 38 that is greater in height than the posterior wall 29, 39 to create or restore lordosis at the vertebral level into which the system of implants 10 is inserted.

The first and second implants 20, 30 also include at least one aperture 26, 36 in the trailing end wall 25, 35 that is dimensioned to receive bone growth promoting material after the implant 20, 30 has been inserted into the disc space. According to the exemplary embodiment shown in FIGS. 1-7, both the first and second implants 20, 30 include visualization apertures 222, 322 in the anterior wall 28, 38 and posterior wall 29, 39 to aid in the visualization of bone growth through the implants 20, 30 at some time after a spinal fusion surgery.

The above described variations in length, height and lordosis, as well as the anti-migration features 27, 37 and radiopaque markers 23, 33 are applicable to all embodiments of the system of spinal fusion implants disclosed herein.

FIGS. 8-13 illustrate a system and method for inserting the system of spinal fusion implants 10 shown in FIGS. 1-7. The first and second implants 20, 30 are inserted into the intervertebral disc space using a single inserter 60. The inserter includes a cannulated outer shaft 61 and an inner shaft 62 that is dimensioned to be received within the cannulated outer shaft 61. As shown in FIGS. 1-7, each of the first and second implants 20, 30 includes a first insertion tool aperture 21, 31 in the leading end wall 24, 34 and aperture 26, 36 in the opposing trailing end wall 25, 35. According to the exemplary embodiment shown in FIGS. 1-13, the first insertion tool aperture 21 in the first implant 20 is threaded to mate with the threaded distal end of the inner shaft 62 of the insertion tool 60.

According to the exemplary embodiment shown in FIGS. 8-13, the inner shaft 62 of the insertion tool 60 is received through the aperture 26 in the trailing end 25 of the first implant 20 and coupled to the first insertion tool aperture 21 in the leading end 24 of the first implant. The cannulated outer shaft 61 may be slid over the inner shaft 62 and engaged with the trailing end 21 of the first implant 20. After appropriate disc removal, the inserter 60 is used to insert the first implant 20 into the intervertebral disc space from a lateral approach and advance the first implant to the distal side of the disc space until it rests on the distal lateral aspect 41 of the inferior vertebral body 40 adjacent the intervertebral disc space. Once the first implant 20 is in the desired position, the outer shaft 61 of the inserter 60 is disengaged from the first implant. The outer shaft 61 of the inserter 60 is then engaged to the trailing end 35 of the second implant 30. The outer shafted 61 coupled to the second implant 30 is slid over the inner shaft 62 of the inserter, wherein the inner shaft 62 of the inserter 60 is received through an aperture 31 in the leading end wall 34 of the second implant 30, through the fusion aperture 32 and through the aperture 36 in the trailing end wall 35 of the second implant. The second implant 30 and outer shaft 61 are advanced along the inner shaft 62 of the inserter and into the disc space until the trailing end wall 35 of the second implant 30 rests on the proximal lateral aspect 42 of the inferior vertebral body 40 adjacent the intervertebral disc space. According to one embodiment, the leading end wall 31 of the second implant 30 abuts the trailing end wall 25 of the first implant 20 when both implants 20, 30 are fully inserted in the disc space. According to an alternative embodiment, the leading end 31 of the second implant 30 is coupled to the trailing end wall 25 of the first implant 20. After the second implant 30 is fully inserted, the inner shaft 62 of the inserter 60 is disengaged from the first implant 20 and the outer shaft 61 of the inserter 60 is disengaged from the second implant 30. At this time, bone growth promoting material may be introduced to the fusion apertures 22, 32 of the first and second implants 20, 30 through the apertures 26, 31, 36 in the trailing ends 25, 35 of the first and second implants 20, 30 and leading end 34 of the second implant.

FIGS. 14-29 illustrate a plurality of alternative embodiments of the system of spinal fusion implants 10 to the embodiment shown in FIGS. 1-13. Each of these alternative embodiments may include all of the features described with respect to the first embodiment, including anti-migration features 27, 37, visualization apertures 222, 322 in the anterior walls 28, 38 and/or posterior walls 29, 39 as well as possible variations in implant length, height and lordosis. The system of implants 10 according to these embodiments may also be inserted according to the above-described method.

Figure 14:
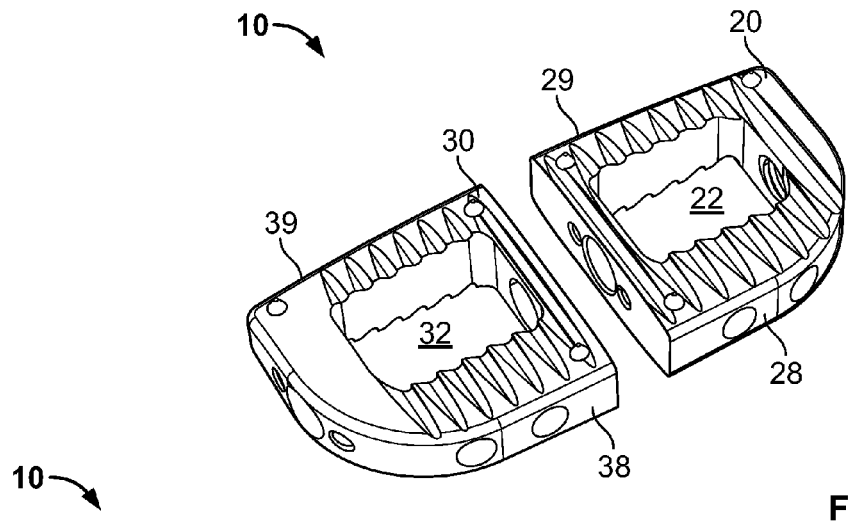
FIG. 14 illustrates a system of implants for promoting fusion across an intervertebral disc space according to an alternative embodiment.

FIG. 14 illustrates an alternative embodiment of the system of spinal fusion implants 10. According to this alternative embodiment, the anterior walls 28, 38 of the first and second implant may have rounded corners.

Figure 15:
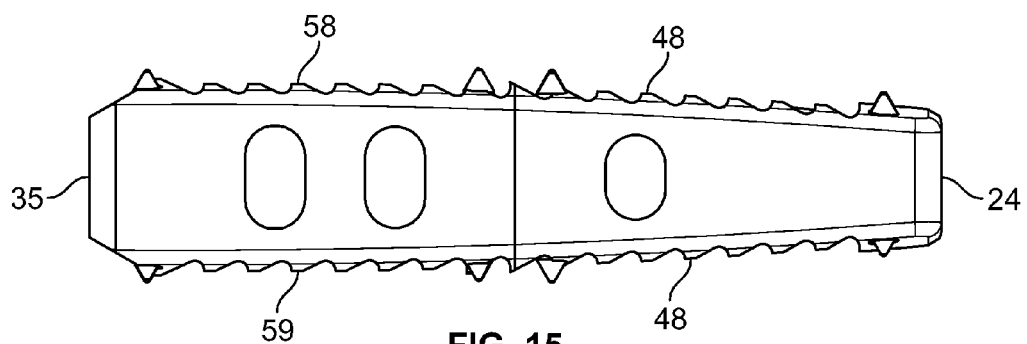
FIG. 15 illustrates a system of implants for promoting fusion across an intervertebral disc space according to a second alternative embodiment.

FIG. 15 illustrates a second alternative embodiment of the system of spinal fusion implants 10. The system according to this embodiment may be used to correct vertebral column deformity in the coronal plane, such that the trailing end walls 25, 35 have a greater height than the leading end walls 24, 34 or vice versa.

Figure 16:
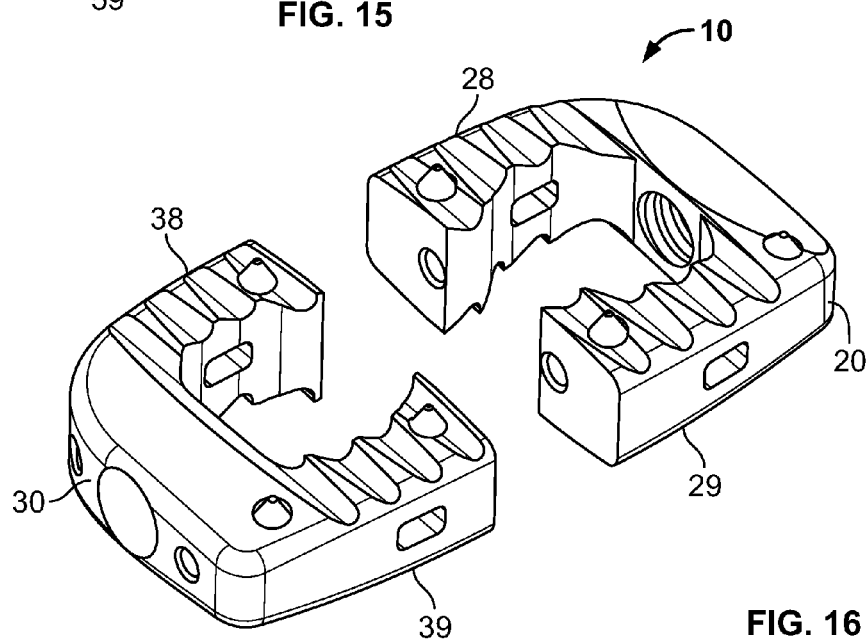
FIG. 16 illustrates a system of implants for promoting fusion across an intervertebral disc space according to a third alternative embodiment.

FIG. 16 illustrates a third alternative embodiment of the system of spinal fusion implants 10 that is dimensioned for use in the thoracic region of the spine. According to this embodiment, the trailing end 25 of the first implant 20 and the leading end 34 of the second implant 30 are open.

Figure 17A:
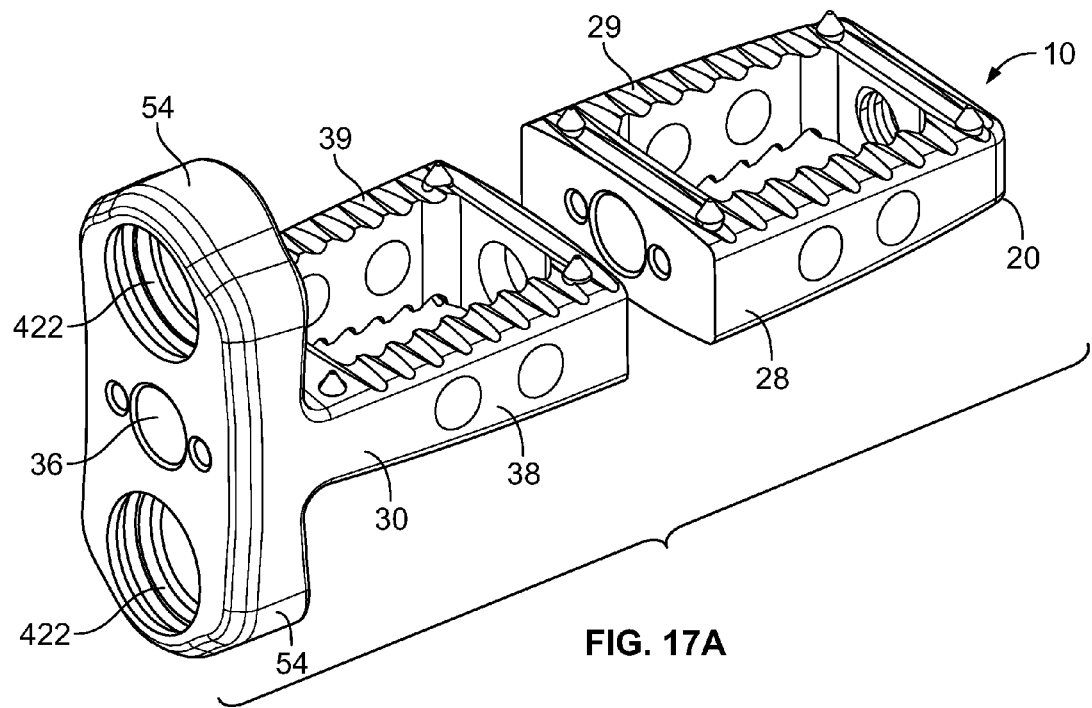
FIGS. 17a-b illustrate a system of implants for promoting fusion across an intervertebral disc space according to fourth alternative embodiment.
Figure 17B:
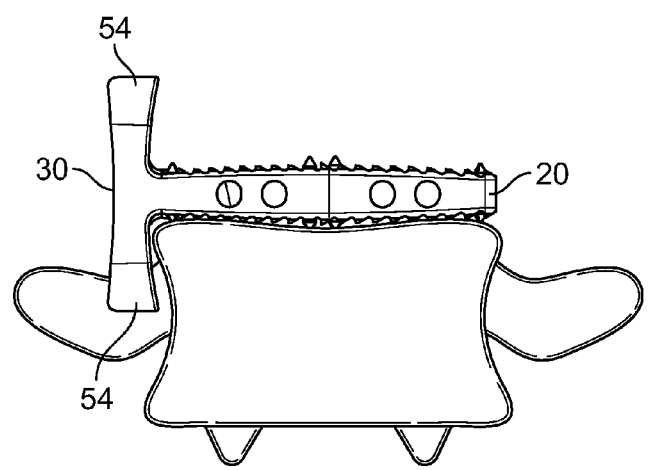

FIGS. 17*a-b* illustrate a fourth alternative embodiment of the system of spinal fusion implants 10 including a fixation element on the trailing end 35 of the second implant 30. The fixation element includes tabs 54 that extend in superior and inferior directions, perpendicular to the second implant 30 and adjacent the lateral aspects of the superior and inferior vertebral bodies, respectively. The tabs 54 include fastener apertures 422 dimensioned to receive bone fasteners (not shown) therethrough.

Figure 18A:
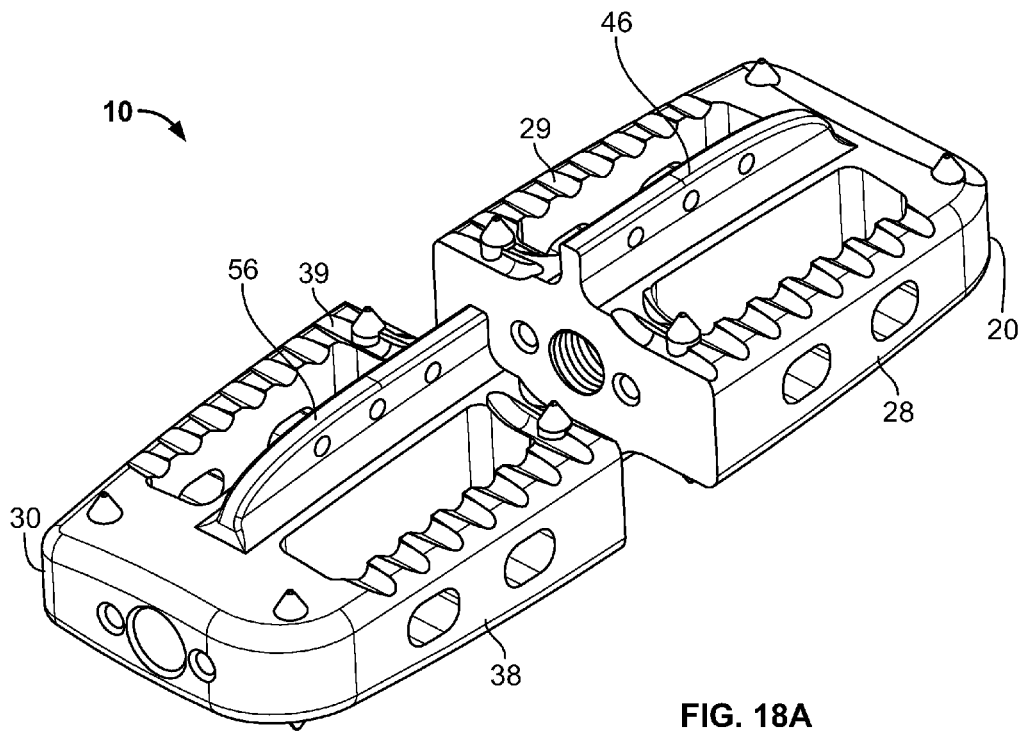
FIGS. 18a-b illustrate a system of implants for promoting fusion across an intervertebral disc space according to fifth alternative embodiment.
Figure 18B:
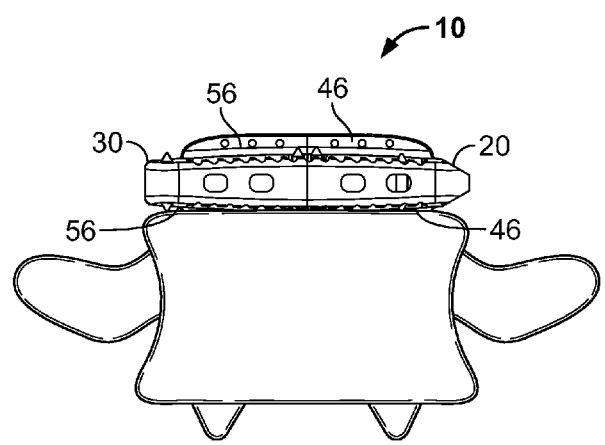

FIGS. 18*a-b* illustrate a fifth alternative embodiment of the system of spinal fusion implants 10 including a keel 46, 56 extending from the top surface 48, 58 and/or bottom surface 49/59 of the first and second implants 20, 30.

Figure 19:
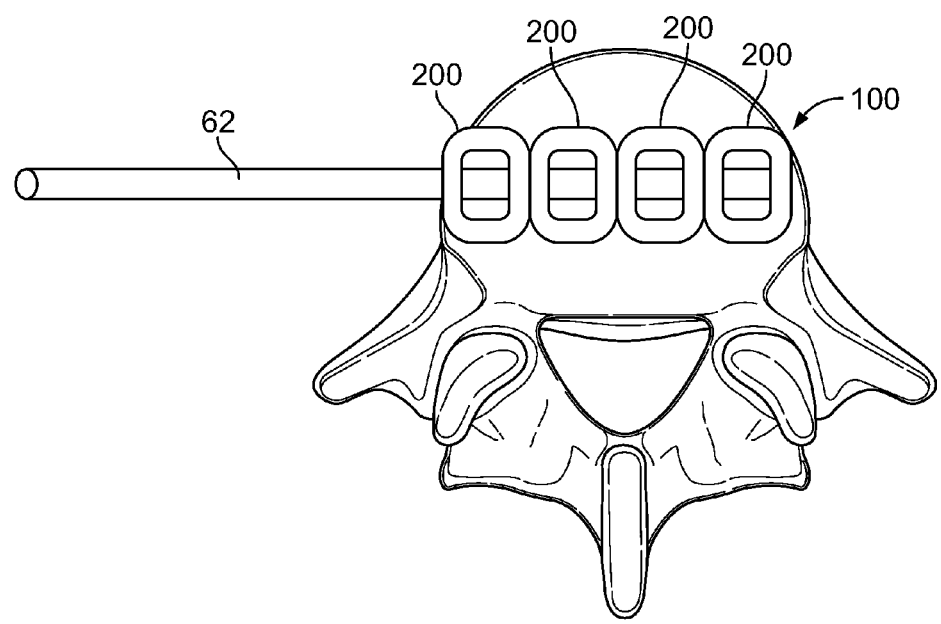
FIG. 19 illustrates a system of implants for promoting fusion across an intervertebral disc space according to a sixth alternative embodiment.

FIG. 19 demonstrates another alternative embodiment of the system of spinal fusion implants 100. According to this embodiment, the system includes a plurality of implants 200 wherein the individual implants 200 may be uniform in length and height, or the implants can vary in length, height or both. According to this embodiment, the implants 200 are configured such that the leading end 224 of the distal implant 200 in the disc space rests on the distal lateral aspect 41 of the inferior vertebral body 40 adjacent the disc space into which the system of implants is inserted, and the trailing end 225 of the proximal implant 200 rests on the proximal lateral aspect 42 of the inferior vertebral body 40.

Figure 20:
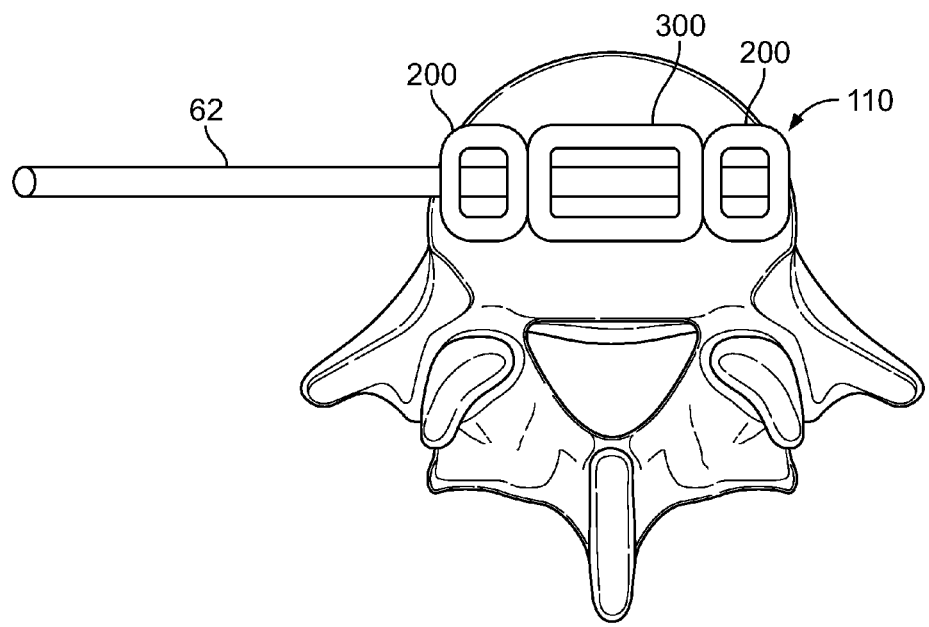
FIG. 20 illustrates a system of implants for promoting fusion across an intervertebral disc space according to a seventh alternative embodiment.

FIG. 20 illustrates a seventh alternative embodiment of the system of spinal fusion implants 110. According to this embodiment, the system 110 includes three implants 200, 300, wherein the proximal and distal implants 200 are uniform in size. The middle implant 300 is one of a variety of lengths to accommodate the width of the disc space, such that the leading end 324 of the middle implant 300 abuts the trailing end 225 of the distal implant and the trailing end 325 of the middle implant abuts the leading end 224 of the proximal implant 200. However, the middle implant has a maximum length that is less than the depth dimension D of the endplate of the inferior vertebral body 40 adjacent the disc space into which the system of spinal fusion implants 110 is inserted. According to one aspect, the middle implant 300 is constructed of bone or bone growth enhancing material.

Figure 21:
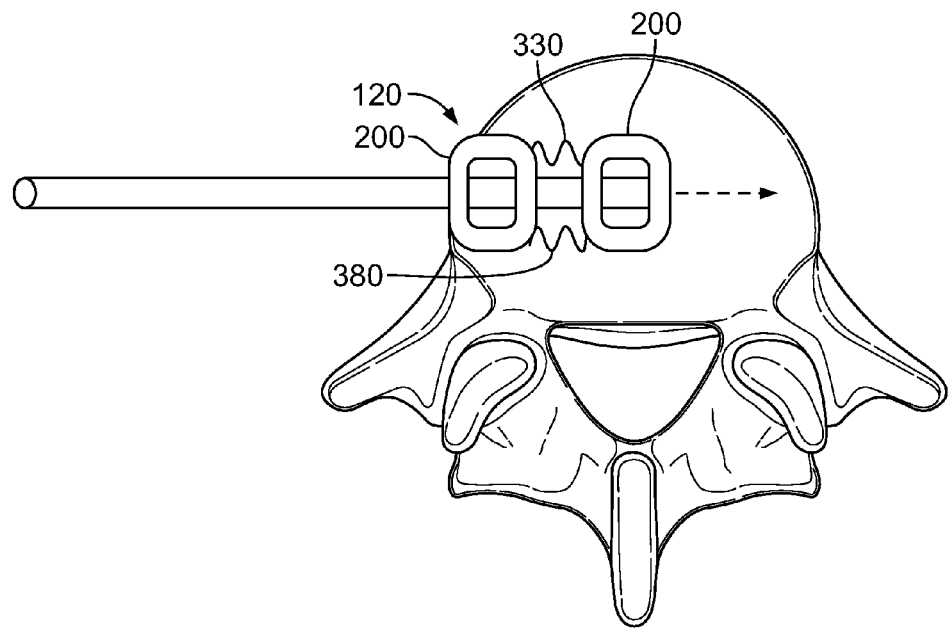
FIGS. 21-22 illustrate a system of implants for promoting fusion across an intervertebral disc space according to an eighth alternative embodiment.
Figure 22:
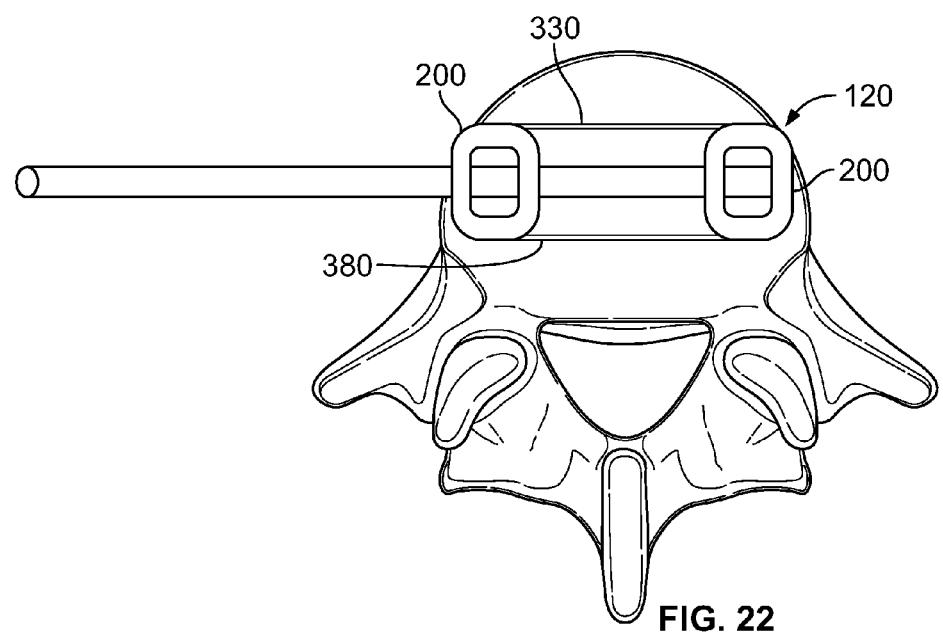

FIGS. 21-22 illustrate an eighth alternative embodiment of the system of spinal fusion implants 120. According to this embodiment, the system includes a pair of implants 200 of uniform size and having a flexible anterior wall 330 and a flexible posterior wall 380 extending between the trailing end 225 of the distal implant 200 and the leading end 324 of the proximal implant 300. As best shown in FIG. 21, the system of implants 120 is inserted into the disc space in a collapsed configuration. Upon insertion, the system of implants 120 is expanded such that the leading end 224 of the distal implant rests on the distal lateral aspect 41 of the inferior vertebral body 40 adjacent the disc space into which the system of implants 120 is inserted, and the flexible anterior and posterior walls 330, 380 are stretched to a taut configuration, as best shown in FIG. 22. After expansion, the inserter 60 is removed from the system of implants 120 and at least the space bordered by the trailing end 225 of the distal implant 200, the leading end 324 of the proximal implant 300 is filled with bone growth promoting material.

Figure 23:
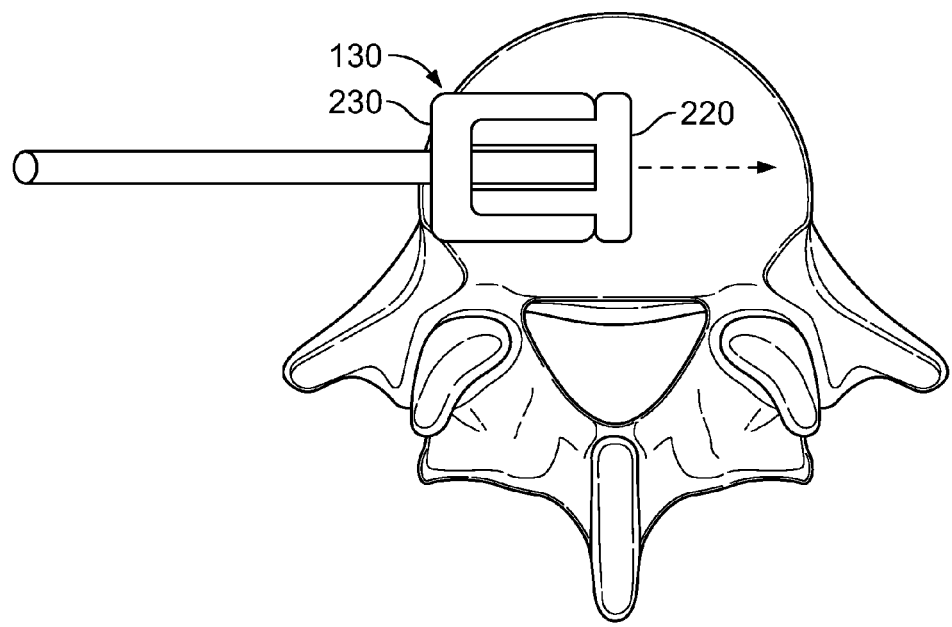
FIGS. 23-26 illustrate a system and method of inserting implants for promoting fusion across an intervertebral disc space according to a ninth embodiment.
Figure 24:
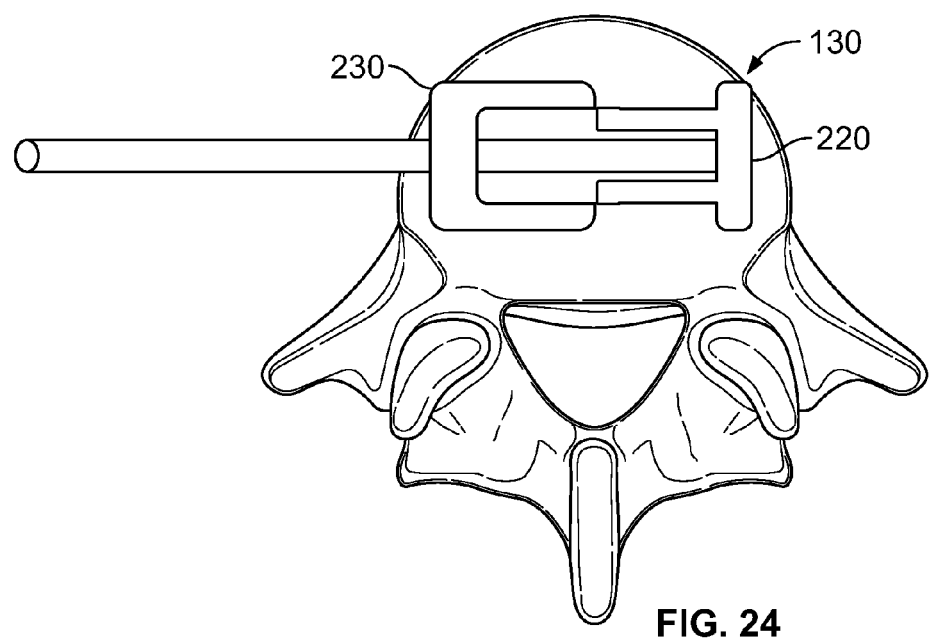
Figure 25:
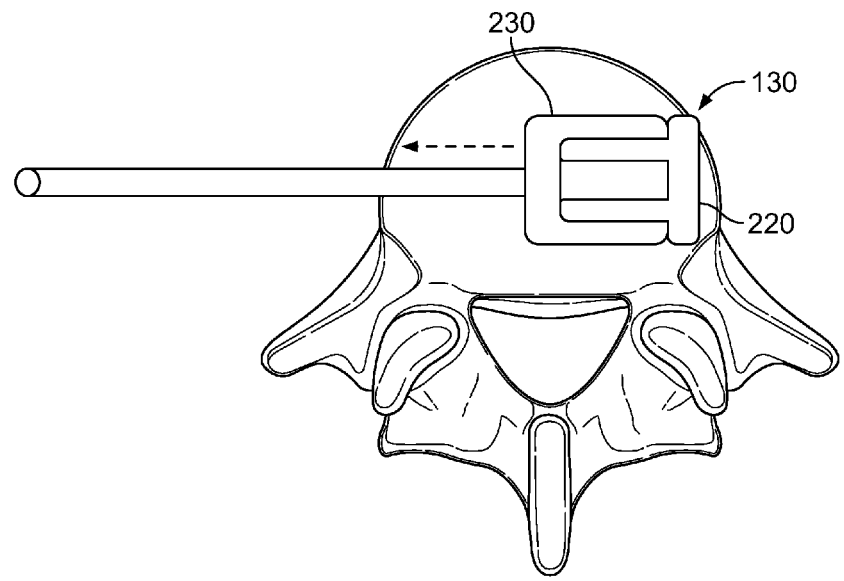
Figure 26:
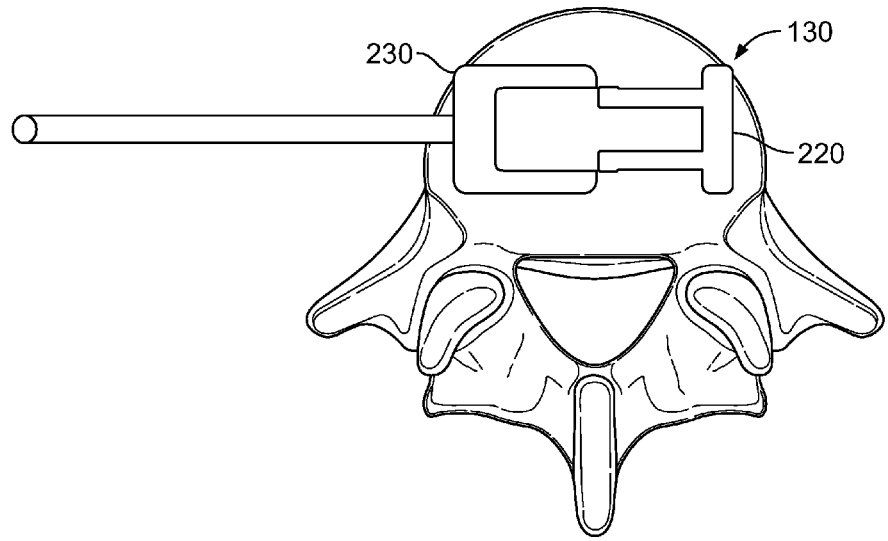

FIGS. 23-26 illustrate a ninth alternative embodiment of the system of spinal fusion implants 130. According to this embodiment, the first implant 220 is nested inside of the second implant 230 during insertion into the disc space. Upon insertion, the nested first and second implants 220, 230 are expanded such that the leading end of the first implant 220 rests on the distal lateral aspect 41 of the vertebral body 40 and the trailing end of the second implant 230 rests on the proximal lateral aspect 42 of the vertebral body 40. The expansion of the system of implants 130 according to this embodiment can be accomplished in two ways. According to one aspect, and as best shown in FIGS. 23-24, the nested first and second implants 220, 230 are inserted into the disc space until the trailing end of the second implant 230 rests on the proximal lateral aspect 42 of the vertebral body 40. Then the inner shaft 62 of the inserter 60 is advance across the disc space, pushing the first implant 220 across the disc space until the leading end of the first implant 220 rests on the distal lateral aspect 41 of the vertebral body 40. Alternatively, the nested first and second implant 220, 230 is inserted until the leading end of the first implant 220 rests on the distal lateral aspect 41 of the vertebral body 40. Then, the inner shaft 62 of the inserter 60 is disengaged from the first implant 220 and the second implant 230 is pulled across the disc space until the trailing end of the second implant 230 rests on the proximal lateral aspect 42 of the vertebral body 40.

Figures 27, 28:
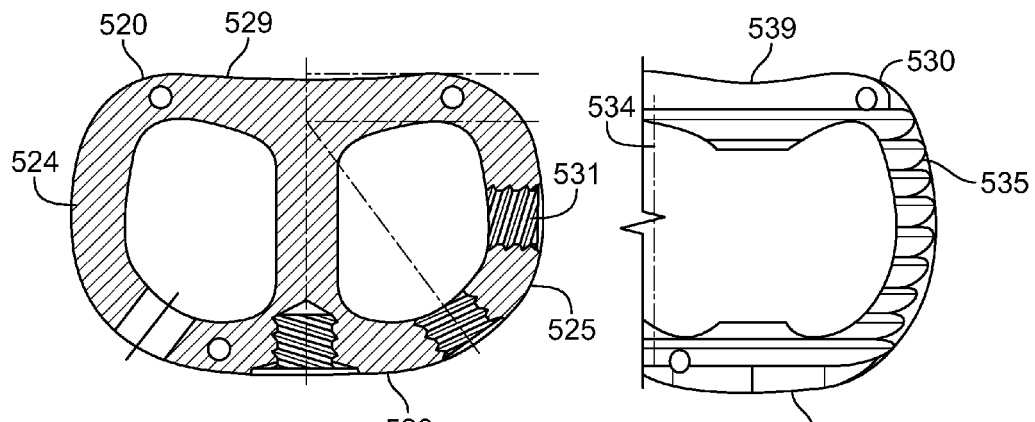
FIGS. 27-29 illustrate a system and method of inserting implants for promoting fusion across an intervertebral disc space according to a tenth embodiment.
Figure 29:
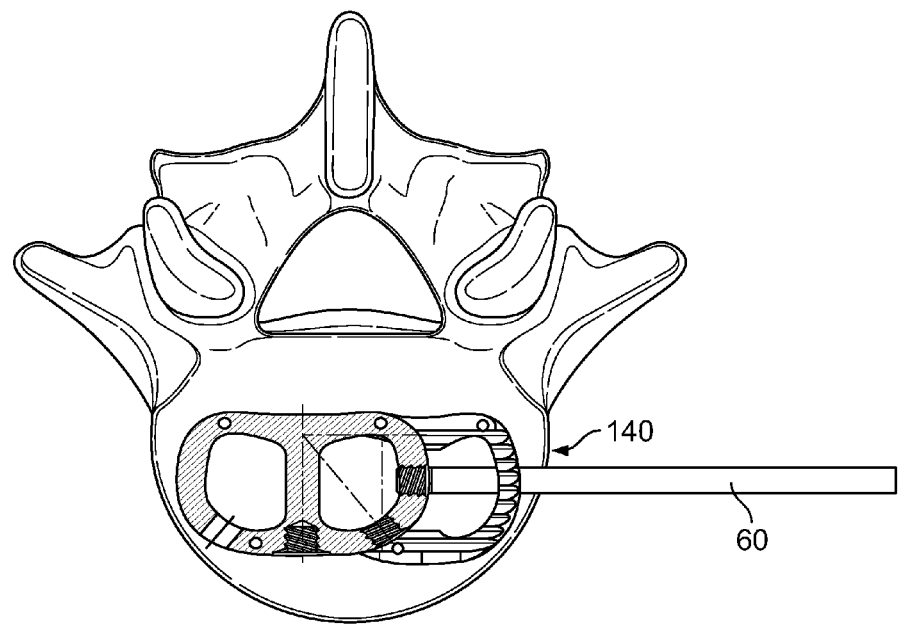

FIGS. 27-29 illustrate a tenth embodiment of the system of spinal fusion implants 140. According to this embodiment, the first implant 520 is dimensioned such that it can inserted via an anterior, anterolateral approach and can support the intervertebral disc space alone, or it can be inserted as part of a system 140 of two implants from a direct lateral approach and be coupled to a lateral inserter via a lateral insertion tool aperture 531. When inserted laterally as part of a two-implant system 140, the leading end 524 of the first implants 520 rests on the distal lateral aspect 41 of the vertebral body 40. Upon insertion of the first implant 520, the second implant 530 is inserted such that the leading end 534 of the second implant 530 abuts the trailing end 525 of the first implant 520. According to another aspect, the leading end 534 of the second implant 530 is coupled to the trailing end 525 of the first implant 520.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A system for promoting fusion across an intervertebral disc space via a lateral approach to the disc space, the disc space located between a superior vertebral body and an inferior vertebral body wherein the interior vertebral body has a width spanning from a first lateral aspect of the inferior vertebral body to a second lateral aspect of the inferior vertebral body, comprising:

a first implant having a leading end wall, a top surface, a bottom surface, an anterior wall, a posterior wall and a trailing end wall extending from the anterior wall to the posterior wall, said first implant having a length between said leading end wall and said trailing end wall, the length of the first implant being less than or equal to half the width of the inferior vertebral body, and having a fusion aperture extending through the top surface and the bottom surface, wherein the trailing end wall further includes a trailing wall aperture in communication with the fusion aperture and configured to receive graft material therethrough while the first implant is positioned within the intervertebral disc space;

a second implant having a trailing end wall, a top surface, a bottom surface, an anterior wall, a posterior wall and a leading end wall extending from the anterior wall to the posterior wall and having a leading wall aperture, said second implant having a length between said leading end wall and said trailing end wall, the length of the second implant being less than or equal to half the width of the inferior vertebral body and having a fusion aperture extending through the top surface and the bottom surface, wherein the trailing end wall further includes an aperture in communication with the fusion aperture and configured to receive graft material therethrough while the second implant is positioned within the intervertebral disc space;

wherein the leading end wall of said first implant rests on the first lateral aspect of the inferior vertebral body and the trailing end wall of the second implant rests on the second lateral aspect of the inferior body, and wherein the leading end wall of the second implant abuts the trailing end wall of the first implant and wherein the trailing wall aperture of the first implant is aligned with the leading wall aperture of the second implant, when the system is tidily inserted in the intervertebral disc space.

2. The system of claim 1, wherein the length of the first implant is equal to the length of the second implant.

3. The system of claim 1, wherein the length of the first implant is greater than the length of the second implant.

4. The system of claim 3, wherein the inferior vertebral body has a depth extending from an anterior aspect of the vertebral body to a posterior aspect of the vertebral body and wherein the length of said first implant is less than the depth of the inferior vertebral body.

5. The system of claim 1, wherein the length of the second implant is greater than the length of the first implant.

6. The system of claim 1, wherein the first implant has a first height extending from said to surface to said bottom surface and the second implant has a second height extending from said top surface to said bottom surface.

7. The system of claim 6, wherein said first height is equal to said second height.

8. The system of claim 6, wherein said first height is greater than said second height.

9. The system of claim 6, wherein said second height is greater than said first height.

\* \* \* \* \*